US00RE46218E

(19) United States
(12) Reissued Patent
Zard et al.

(10) Patent Number: US RE46,218 E
(45) Date of Reissued Patent: Nov. 29, 2016

(54) PROCESS FOR THE SYNTHESIS OF AGOMELATINE

(71) Applicant: LES LABORATOIRES SERVIER, Suresnes (FR)

(72) Inventors: Samir Zard, Gif-sur-Yvette (FR); Béatrice Sire, Palaiseau (FR); Mehdi Boumediene, Choisy le Roi (FR)

(73) Assignee: LES LABORATOIRES SERVIER, Suresnes (FR)

(21) Appl. No.: 14/619,284

(22) Filed: Feb. 11, 2015

Related U.S. Patent Documents

Reissue of:
(64) Patent No.: 8,853,449
Issued: Oct. 7, 2014
Appl. No.: 13/977,799
PCT Filed: Jan. 4, 2012
PCT No.: PCT/FR2012/000005
§ 371 (c)(1),
(2) Date: Jul. 1, 2013
PCT Pub. No.: WO2012/113999
PCT Pub. Date: Aug. 30, 2012

(30) Foreign Application Priority Data

Jan. 5, 2011 (FR) ..... 11 00024

(51) Int. Cl.

| | |
|---|---|
| ***C07C 231/06*** | (2006.01) |
| ***C07C 255/33*** | (2006.01) |
| ***C07C 231/02*** | (2006.01) |
| ***C07C 233/18*** | (2006.01) |
| ***C07C 253/30*** | (2006.01) |
| ***C07C 255/37*** | (2006.01) |
| ***C07C 255/40*** | (2006.01) |

(52) U.S. Cl.
CPC ..... *C07C 231/02* (2013.01); *C07C 231/06* (2013.01); *C07C 233/18* (2013.01); *C07C 253/30* (2013.01); *C07C 255/37* (2013.01); *C07C 255/40* (2013.01); *C07C 2102/10* (2013.01)

(58) Field of Classification Search
CPC . C07C 231/02; C07C 231/06; C07C 233/18; C07C 253/30; C07C 255/37; C07C 255/40; C07C 2102/10
USPC ..... 564/124, 130; 558/426, 428, 430
See application file for complete search history.

(56) References Cited

U.S. PATENT DOCUMENTS

| | | | |
|---|---|---|---|
| 5,318,994 | A | 6/1994 | Andrieux et al. |
| 7,544,839 | B2 | 6/2009 | Souvie et al. |
| 2005/0182267 | A1 | 8/2005 | Souvie et al. |

FOREIGN PATENT DOCUMENTS

| | | |
|---|---|---|
| CN | 101486665 | 7/2009 |
| EP | 0447285 | 9/1991 |
| EP | 1564202 | 8/2005 |

OTHER PUBLICATIONS

International Preliminary Report on Patentability/Written Opinion for PCT/FR2012/000005 of Jul. 10, 2013.
Chu et al., Synthetic Communications 31(4), 2001, 621-629.
Liard et al., Tetrahedron Letters 38(10), 1997, 1759-1762.
Kalinin et al., Journal of Organometallic Chemistry 383, 1990, 85-91.
International Search Report for PCT/FR2012/000005 of Mar. 8, 2012.
International Preliminary Report on Patentability Written Opinion for PCT/FR2012/000005, 2012.

*Primary Examiner* — Gary Kunz
(74) *Attorney, Agent, or Firm* — Hueschen and Sage

(57) ABSTRACT

Process for the industrial synthesis of the compound of formula (I)

(I)

17 Claims, No Drawings

PROCESS FOR THE SYNTHESIS OF AGOMELATINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a 371 of PCT/FR12/00005, filed Jan. 4, 2012.

The present invention relates to a new process for the industrial synthesis of agomelatine, or N-[2-(7-methoxy-1-naphthyl)ethyl]acetamide, of formula (I):

(I)

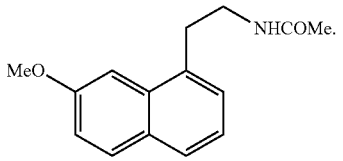

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-$HT_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European patent specifications EP 0 447 285 and EP 1 564 202.

In view of the pharmaceutical value of this compound, it has been important to be able to produce it using an effective industrial synthesis process which is readily transferable to the industrial scale and which provides agomelatine in a good yield and with excellent purity.

Patent specification EP 0 447 285 describes production of agomelatine in eight steps starting from 7-methoxy-1-tetralone.

In patent specification EP 1 564 202, the Applicant developed a new, much more effective and industrialisable synthesis route in only four steps starting from 7-methoxy-1-tetralone that makes it possible to obtain agomelatine in highly reproducible manner in a well-defined crystalline form.

However, the search for new synthesis routes, especially starting from starting materials that are less costly than 7-methoxy-1-tetralone, is currently still relevant.

The Applicant has continued his investigations and has developed a new process for the synthesis of agomelatine starting from allyl cyanide and a xanthate compound: these new starting materials have the advantage of being simple and readily obtainable in large quantities at less cost.

This synthesis route is based on carrying out free radical reactions that are not very commonly used but are nevertheless very effective. Converting these reactions to the industrial scale using continuous-flow reactors is promising as it becomes simpler to control propagation of the chain reaction.

This new process moreover makes it possible to obtain agomelatine in reproducible manner and without requiring laborious purification, with a purity that is compatible with its use as a pharmaceutical active ingredient. Indeed, agomelatine can accordingly be synthesised in 6 steps in the course of which only two of the intermediates are isolated.

More specifically, the present invention relates to a process for the industrial synthesis of the compound of formula (I):

(I)

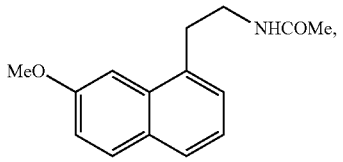

which process is characterised in that allyl cyanide of formula (II):

(II)

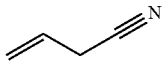

is reacted, in the presence of a free radical initiator, with a compound of formula (III):

(III)

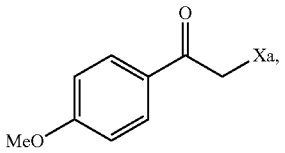

wherein Xa represents a group —S—C(S)—OR in which R represents a linear or branched ($C_1$-$C_6$)alkyl group, to yield the compound of formula (IV):

(IV)

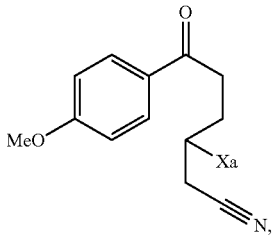

wherein Xa is as defined hereinbefore, it being possible for this latter compound optionally to be isolated, before being subjected to a cyclisation reaction in the presence of a free radical initiator in order to form the compound of formula (V):

(V)

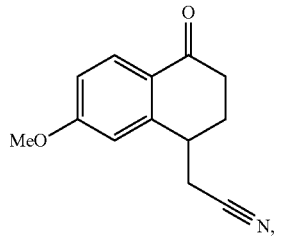

which compound of formula (V) also optionally may be isolated, which is subjected to a reduction-dehydration reaction to yield the compound of formula (VI):

(VI)

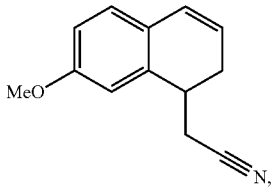

which is then subjected to an aromatisation reaction to yield the compound of formula (VII):

(VII)

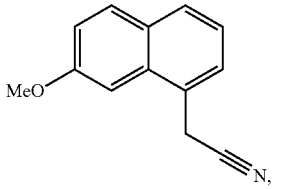

which is subjected to reduction using hydrogen in the presence of Raney nickel in a polar protic medium and to reaction with acetic anhydride to yield the compound of formula (I), which is isolated in the form of a solid.

In a preferred embodiment of the invention, the compound of formula (VII) is then subjected to reduction using hydrogen in the presence of Raney nickel in an ammoniacal ethanol medium and then converted into a salt using hydrochloric acid to yield the compound of formula (VIII):

(VIII)

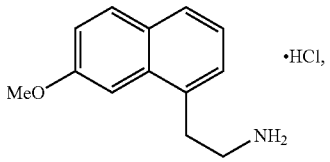

which is successively subjected to the action of sodium acetate and then acetic anhydride to yield the compound of formula (I), which is isolated in the form of a solid.

Alternatively, the compound of formula (VII) can be subjected to reduction by hydrogen in the presence of Raney nickel in a medium comprising acetic anhydride in a polar protic medium to yield the compound of formula (I), which is isolated in the form of a solid.

In a preferred compound of formula (III), Xa represents a group —S—C(S)—$OC_2H_5$.

In the processes according to the invention, initiation of the free radical reactions is carried out by thermal means. Preferably, the reaction mixture is heated to a temperature of from 50° C. to 140° C. Even more preferably, cyclisation is carried out at a temperature of from 130 to 135° C.

Peroxides are free radical initiators that are especially suitable for carrying out the step of addition of the compound of formula (II) to the compound of formula (III), or for performing cyclisation of the compound of formula (IV) to form the compound of formula (V). By way of example, there may be mentioned, especially, diisobutyryl peroxide, cumyl peroxyneodecanoate, tert-amyl peroxyneodecanoate, di(2-ethylhexyl)peroxydicarbonate, tert-butyl peroxyneodecanoate, dibutyl peroxydicarbonate, dicetyl peroxydicarbonate, dimyristyl peroxydicarbonate, tert-butyl peroxyneoheptanoate, tert-amyl peroxypivalate, didecanoyl peroxide, tert-amyl peroxy-2-ethylhexanoate, tert-butyl peroxyisobutyrate, 1,4-di(tert-butylperoxycarbo)cyclohexane, tert-butyl peroxyacetate, tert-butyl peroxybenzoate, di-tert-amyl peroxide, tert-butyl cumyl peroxide, bis(tert-butyl)peroxide, dicumyl peroxide, dilauroyl peroxide (DLP) or di(4-tert-butylcyclohexyl)peroxydicarbonate.

Preferably, the reaction is initiated in the presence of dilauroyl peroxide.

The amount of dilauroyl peroxide used in the cyclisation is preferably from 1 to 2.5 equivalents.

In a preferred embodiment of the invention, dilauroyl peroxide is added to the medium in stages.

The addition and/or cyclisation reactions are carried out in a solvent customarily used in free radical chemistry such as 1,2-dichloroethane, dichloromethane, benzene, toluene, trifluoromethylbenzene, chlorobenzene, hexane, cyclohexane, heptane, octane, ethyl acetate, tert-butyl alcohol, and mixtures thereof.

Preference is given to using ethyl acetate in the step of addition of the compound of formula (II) to the compound of formula (III), whilst cyclisation of the compound of formula (IV) to form the compound of formula (V) is advantageously carried out in chlorobenzene, ethyl acetate or ethyl butyrate. In this latter reaction, chlorobenzene is more especially preferred.

Conversion of the compound of formula (V) into the compound of formula (VI) is advantageously carried out in the presence of a Lewis acid such as aluminium isopropoxide or samarium isopropoxide. This conversion is moreover preferably carried out in an alcohol (primary or secondary), and even more preferably in isopropanol.

Preferably, a catalytic amount of p-toluenesulphonic acid is added to the mixture once all the tetralone (V) has been consumed at the end of conversion of the compound of formula (V) into the compound of formula (VI).

Aromatisation of compound (VI) is carried out in the presence of a quinone, preferably in the presence of 2,3-dichloro-5,6-dicyano-1,4-benzoquinone (DDQ) or tetrachlorobenzoquinone (TCQ). Even more preferably, aromatisation is carried out in the presence of TCQ at the reflux of toluene.

The compound of formula (II) is accessible to the person skilled in the art by means of conventional chemical reactions and/or chemical reactions described in the literature.

This process is especially valuable for the following reasons:

- it makes it possible to obtain the compound of formula (I) on an industrial scale in good yields, starting from a simple, low-cost starting material;
- only the intermediates of formulae (VI) and (VII) require a purification and isolation step.

The compounds of formulae (V) and (VI) obtained according to the process of the invention are new and useful as intermediates in the synthesis of agomelatine.

The Examples hereinbelow illustrate the invention without limiting it in any way. For the purpose of validating the reaction route, the synthesis intermediates were systematically isolated and characterised. However, it is possible to considerably optimise the procedures by limiting the number of intermediates isolated. Accordingly, Example 2 given hereinbelow corresponds to the same reaction route as that used in Example 1 but with the difference that only (7-methoxy-1,2-dihydro-1-naphthyl)acetonitrile and (7-methoxy-1-naphthyl)acetonitrile were isolated.

EXAMPLE 1

N-[2-(7-Methoxy-1-naphthyl)ethyl]acetamide

Step A: S-[1-(cyanomethyl)-4-(4-methoxyphenyl)-4-oxobutyl]-O-ethyl dithiocarbonate A solution of allyl cyanide (4.8 mL, 60.0 mmol) and S-[2-(4-methoxyphenyl)-2-oxoethyl]-O-ethyl dithiocarbonate[1] (8.1 g, 30.0 mmol) in ethyl acetate (30 mL) is heated at reflux for 15 minutes under a nitrogen atmosphere. There is added, firstly, an amount of dilauroyl peroxide (10 mol %) to the solution under reflux. After 1 hour 30 minutes, another amount of dilauroyl peroxide (5 mol %) is also introduced. When the reagents have been completely consumed, the mixture is cooled to ambient temperature and concentrated under reduced pressure. The crude mixture is then purified by flash column chromatography (petroleum ether-ethyl acetate: 95-5 to 80-20) to yield the title compound in the form of an oil in a yield of 98%.

[1]S-[2-(4-methoxyphenyl)-2-oxoethyl]-O-ethyl dithiocarbonate is obtained according to the protocol described in Batanero, B. et al., J. Org. Chem. 2001, 66, 320.

$^1$H NMR (δ, ppm) 7.93 (m, 2H, CH-4), 6.93 (m, 2H, CH-3), 4.67-4.57 (m, 2H, $CH_2$-13), ($CDCl_3$, 400 MHz) 3.99 (m, 1H, CH-9), 3.87 (s, 3H, $CH_3$-1), 3.15 (t, 2H, J=7.3 Hz, $CH_2$-7), 2.95 (dd, 2H, J=17.0, 6.0 Hz, $CH_2$-10), 2.41-2.31 (m, 1H, $CH_2$-8), 2.19-2.08 (m, 1H, $CH_2$-8), 1.41 (t, 3H, J=7.1 Hz, $CH_3$-14).

Step B: (7-Methoxy-4-oxo-1,2,3,4-tetrahydro-1-naphthyl)acetonitrile

The compound of Step A, used directly without having been purified, is redissolved in chlorobenzene (900 mL) and the solution is refluxed for 15 minutes under a nitrogen atmosphere. Dilauroyl peroxide is then gradually added to the solution under reflux (10 mol % every 10 minutes). When the reaction is complete, the mixture is cooled to ambient temperature and concentrated under reduced pressure. Acetonitrile is then introduced in order to cause a large part of the dilauroyl peroxide compounds to precipitate out. The mixture is then filtered, concentrated under reduced pressure and purified by flash column chromatography (petroleum ether-ethyl acetate: 60-40) to yield the title compound in solid form in a yield of 40%.

HRMS (EI, m/z) Calc. for $C_{13}H_{13}NO_2$: 215.0946; found: 215.0946.

Step C: (7-Methoxy-1,2-dihydro-1-naphthyl)acetonitrile

Aluminium isopropoxide (2.05 g, 10.0 mmol) is added to a solution of the compound obtained in Step B (680 mg, 3.15 mmol) in isopropanol (15 mL) at ambient temperature. The reaction mixture is refluxed. When the reagents have been completely consumed, a few crystals of p-toluenesulphonic acid monohydrate are added and a Dean-Stark apparatus is mounted on top of the flask. The mixture is again refluxed for 1 hour, during which the isopropanol is gradually replaced with toluene by means of the Dean-Stark apparatus. A 1N HCl solution is then added and the resulting phases are separated. The aqueous phase is extracted with ethyl acetate, the organic phases being washed with saturated $NaHCO_3$ solution and with saturated NaCl solution, then dried over $MgSO_4$, filtered and concentrated under reduced pressure. The residue is purified by column chromatography (petroleum ether-ethyl acetate: 80-20) to yield the title product in the form of an oil in a yield of 85%.

HRMS (EI, m/z) Calc. for $C_{13}H_{13}NO$: 199.0997. found: 199.1001.

Step D: (7-Methoxy-1-naphthyl)acetonitrile

Method A:

To a solution of the compound obtained in Step C (1.0 g, 5.0 mmol) in dichloromethane (50 mL) at ambient temperature there is added DDQ (1.4 g, 6.0 mmol). The reaction mixture is stirred for 2 days and is then washed with saturated $NaHCO_3$ solution. The aqueous phase is extracted with ethyl acetate, the organic phase being washed with saturated NaCl solution, dried over $MgSO_4$, filtered and concentrated under reduced pressure. The residue is purified by column chromatography (petroleum ether-ethyl acetate: 80-20) to yield the title product in solid form in a yield of 55%.

Method B:

To a solution of TCQ (615 mg, 2.5 mmol) in toluene (1.5 mL) heated to 80° C. there is added the compound obtained in Step C (462 mg, 2.3 mmol) dissolved in toluene (3.5 mL). The mixture is then refluxed for 2.5 hours and is then diluted with water and extracted with petroleum ether. The organic phase is washed with NaOH solution (30% by weight) and with water and is then dried over $MgSO_4$, filtered and concentrated under reduced pressure. The residue is purified by column chromatography (petroleum ether-ethyl acetate: 80-20) to yield the title product in solid form in a yield of 61%.

HRMS (EI, m/z) Calc. for $C_{13}H_{11}NO$: 197.0841. found: 197.0838.

Step E: N-[2-(7-Methoxy-1-naphthyl)ethyl]acetamide

The reaction was carried out on a larger batch in order to optimise the yield obtained: 136 g of Raney nickel, 2.06 L of ethanol and 0.23 L of water are introduced into an 8 L reactor. Whilst stirring at 70° C. and under 30 bars of hydrogen, the compound obtained in Step D (0.8 kg) dissolved in acetic anhydride (2.4 L) is slowly added. At the end of the addition, the reaction mixture is stirred for 1 hour under hydrogen at 30 bar, the reactor is then decompressed and the liquors are filtered. After concentration of the mixture, the residue is crystallised from a mixture of ethanol/water 35/65 to yield the title product in a yield of 89% and with a chemical purity greater than 99%.

Melting point: 108° C.

EXAMPLE 2

N-[2-(7-ethoxy-1-naphthyl)ethyl]acetamide

Step A:
(7-Methoxy-1,2-dihydro-1-naphthyl)acetonitrile

A solution of allyl cyanide (6.75 mL, 84.0 mmol) and S-[2-(4-methoxyphenyl)-2-oxoethyl]-O-ethyl dithiocarbonate[1] (11.3 g, 42.0 mmol) in ethyl acetate (45 mL) is heated at reflux for 15 minutes under a nitrogen atmosphere. There is added, firstly, an amount of dilauroyl peroxide (10 mol %) to the solution under reflux. After 1 hour 30 minutes, another amount of dilauroyl peroxide (5 mol %) is also introduced. When the reagents have been completely consumed, the mixture is cooled to ambient temperature and concentrated under reduced pressure. The crude mixture is redissolved in chlorobenzene (640 mL) and the solution is refluxed for 15 minutes under a nitrogen atmosphere. Dilauroyl peroxide is then gradually added to the solution under reflux (10 mol % every 10 minutes). When the reaction is complete, the mixture is cooled to ambient temperature and concentrated under reduced pressure. Acetonitrile is then introduced in order to cause a large part of the dilauroyl peroxide compounds to precipitate out. The mixture is then filtered and concentrated under reduced pressure. Half the crude oil thereby obtained is redissolved in isopropanol (100 mL) at ambient temperature in the presence of aluminium isopropoxide (13.6 g, 66.6 mmol). The reaction mixture is refluxed. When the reagents have been completely consumed, a few crystals of p-toluenesulphonic acid monohydrate are added and a Dean-Stark apparatus is mounted on top of the flask. The mixture is again refluxed for 2 hours, during which the isopropanol is gradually replaced with toluene by means of the Dean-Stark apparatus. A 1N HCl solution is then added and the resulting phases are separated. The aqueous phase is extracted with ethyl acetate, the organic phases being washed with saturated $NaHCO_3$ solution and with saturated NaCl solution, then dried over $MgSO_4$, filtered and concentrated under reduced pressure. The residue is purified by column chromatography (petroleum ether-ethyl acetate: 80-20) to yield the title product in the form of an oil in a yield of 24%.

HRMS (EI, m/z) Calc. for $C_{13}H_{13}NO$: 199.0997. found: 199.1001.

Step B: (7-Methoxy-1-naphthyl)acetonitrile

The procedure is analogous to Step D of Example 1.

Step C:
N-[2-(7-Methoxy-1-naphthyl)ethyl]acetamide

The procedure is analogous to Step E of Example 1.

The invention claimed is:

1. A process for the synthesis of a compound of formula (I):

(I)

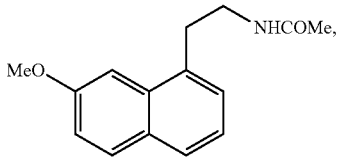

wherein allyl cyanide of formula (II):

(II)

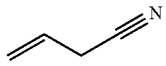

is reacted, in the presence of a free radical initiator, with a compound of formula (III):

(III)

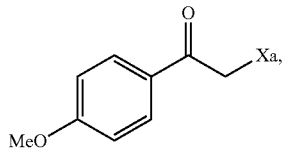

wherein Xa represents a group —S—C(S)—OR in which R represents a linear or branched ($C_1$-$C_6$)alkyl group, to yield the compound of formula (IV):

(IV)

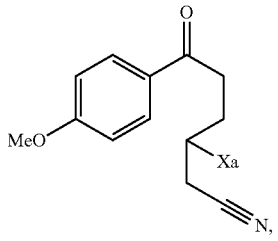

wherein Xa is as defined hereinbefore, wherein this latter compound may be optionally isolated, before being subjected to a cyclisation reaction in the presence of a free radical initiator in order to form the compound of formula (V):

(V)

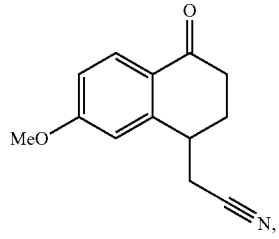

which compound of formula (V) may also be optionally isolated, which compound of formula (V) is subjected to a reduction-dehydration reaction to yield the compound of formula (VI):

(VI)

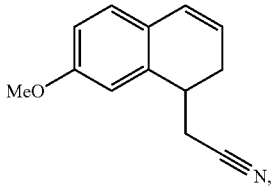

which is then subjected to an aromatisation reaction to yield the compound of formula (VII):

(VII)

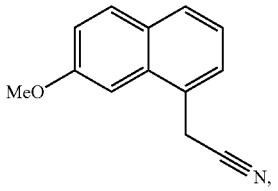

which is subjected to reduction using hydrogen in the presence of Raney nickel in a polar protic medium and to reaction with acetic anhydride to yield the compound of formula (I), which is isolated in the form of a solid.

2. The process according to claim 1, wherein the compound of formula (VII) is subjected to reduction using hydrogen in the presence of Raney nickel in an ammoniacal ethanol medium and then converted into a salt using hydrochloric acid to yield the compound of formula (VIII):

(VIII)

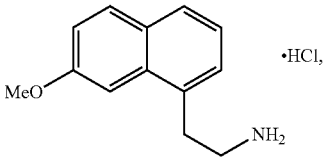

which is successively subjected to the action of sodium acetate and then acetic anhydride to yield the compound of formula (I), which is isolated in the form of a solid.

3. The process according to claim 1, wherein the compound of formula (VII) is subjected to reduction by hydrogen in the presence of Raney nickel in a medium comprising acetic anhydride in a polar protie medium to yield the compound of formula (I), which is isolated in the form of a solid.

4. The process according to claim 1, wherein the group Xa represents —S—C(S)—$OC_2H_5$.

5. The process according to claim 1, wherein the free radical reactions are initiated by thermal means at a temperature of from 50 to 140° C.

6. The process according to claim 1, wherein cyclisation of the compound of formula (IV) is carried out at a temperature of from 130 to 135° C.

7. The process according to claim 1, wherein the step of addition of the compound of formula (II) to the compound of formula (III) and that of cyclisation of the compound of formula (IV) are initiated in the presence of dilauroyl peroxide.

8. The process according to claim 1, wherein the step of addition of the compound of formula (II) to the compound of formula (III) is carried out in chlorobenzene.

9. The process according to claim 1, wherein the step of cyclisation of the adduct of formula (IV) to form the compound of formula (V) is carried out in ethyl acetate.

10. The process according to claim 1, wherein the conversion of the compound of formula (V) into the compound of formula (VI) is carried out in the presence of aluminium isopropoxide.

11. The process according to claim 1, wherein the conversion of the compound of formula (V) into the compound of formula (VI) is carried out in isopropanol.

12. The process according to claim 1, wherein a catalytic amount of p-toluenesulphonic acid is added to the mixture at the end of conversion of the compound of formula (V) into the compound of formula (VI).

13. The process according to claim 1, wherein the aromatisation of the compound of formula (VI) is carried out in the presence of a quinone.

14. The process according to claim 1, wherein the aromatisation of the compound of formula (VI) is carried out in the presence of TCQ at the reflux of toluene.

15. A process for the synthesis of agomelatine starting from the compound of formula (V):

(V)

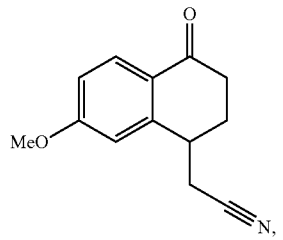

wherein the compound of formula (V) is obtained according to the process according to claim 1.

16. A process for the synthesis of agomelatine starting from the compound of formula (VI):

(VI)

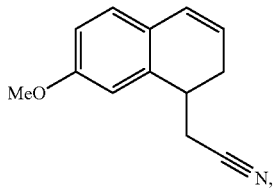

wherein the compound of formula (VI) is obtained according to the process according to claim 1.

[17. A compound of formula (V):
(V)
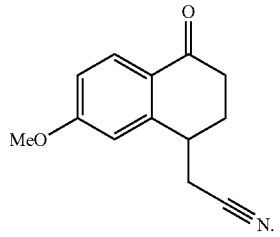
]
*18. A compound of formula (VI):*
*(VI)*
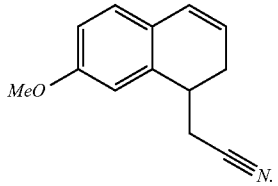
* * * * *